United States Patent
Poxon et al.

(10) Patent No.: US 8,968,768 B2
(45) Date of Patent: Mar. 3, 2015

(54) PHYTOSTEROL NUTRITIONAL SUPPLEMENTS

(75) Inventors: Scott W. Poxon, Mechanicsville, VA (US); William Bubnis, Mechanicsville, VA (US); Bruce W. Sutton, Richmond, VA (US); Jeffrey V. Vernon, Fredericksburg, VA (US); Denise L. Walters, Richmond, VA (US); Michael G. Williams, Midlothian, VA (US); Neil Wittenberg, Randolph, NJ (US)

(73) Assignee: Wyeth LLC, New York, NY (US)

( * ) Notice: Subject to any disclaimer, the term of this patent is extended or adjusted under 35 U.S.C. 154(b) by 194 days.

(21) Appl. No.: 11/236,570

(22) Filed: Sep. 28, 2005

(65) Prior Publication Data

US 2006/0024352 A1  Feb. 2, 2006

Related U.S. Application Data

(63) Continuation-in-part of application No. 11/090,486, filed on Mar. 28, 2005, now abandoned.

(60) Provisional application No. 60/557,247, filed on Mar. 29, 2004.

(51) Int. Cl.
*A61K 47/00* (2006.01)
*A61K 31/56* (2006.01)
(Continued)

(52) U.S. Cl.
CPC ............... *A61K 31/56* (2013.01); *A23L 1/3004* (2013.01); *A23L 1/302* (2013.01); *A23L 1/304* (2013.01); *A61K 9/0056* (2013.01); *A61K 9/009* (2013.01); *A61K 9/10* (2013.01); *A61K 9/2018* (2013.01); *A61K 9/2054* (2013.01); *A61K 9/4866* (2013.01); *A61K 31/355* (2013.01); *A61K 31/375* (2013.01); *A61K 31/51* (2013.01); *A61K 31/525* (2013.01); *A61K 31/714* (2013.01); *A61K 45/06* (2013.01); *A61K 47/02* (2013.01); *A23V 2002/00* (2013.01); *A61K 9/1611* (2013.01); *A61K 9/1652* (2013.01)
USPC ........................................................ 424/439

(58) Field of Classification Search
USPC ........................................................ 424/439
See application file for complete search history.

(56) References Cited

U.S. PATENT DOCUMENTS 3,758,690 A  *  9/1973  Gittos et al. .................. 514/657
3,881,005 A       4/1975  Thakkar et al.
(Continued)

FOREIGN PATENT DOCUMENTS

WO   WO 2004/026233   *  4/2004

OTHER PUBLICATIONS

Endur.com, Phytosterols—Immediate Release, Last Accessed May 19, 2009, www.endure.com.*

(Continued)

*Primary Examiner* — Trevor Love
(74) *Attorney, Agent, or Firm* — Maureen P. O'Brien; Jeffrey M. Gold

(57) ABSTRACT

The invention provides a nutritional supplement which includes phytosterol to facilitate reduction of cholesterol. The nutritional supplement may be a swallowable tablet, chewable tablet, sachet, capsule or suspension. The invention further provides a method for tableting one fourth to one half of the daily effective dosage of a phytosterol containing nutritional supplement in a practical sized swallowable tablet and a method for reducing blood cholesterol in humans.

11 Claims, 3 Drawing Sheets

(51) Int. Cl.

| | | |
|---|---|---|
| A23L 1/30 | (2006.01) | |
| A23L 1/302 | (2006.01) | |
| A23L 1/304 | (2006.01) | |
| A61K 9/00 | (2006.01) | |
| A61K 9/10 | (2006.01) | |
| A61K 9/20 | (2006.01) | |
| A61K 9/48 | (2006.01) | |
| A61K 31/355 | (2006.01) | |
| A61K 31/375 | (2006.01) | |
| A61K 31/51 | (2006.01) | |
| A61K 31/525 | (2006.01) | |
| A61K 31/714 | (2006.01) | |
| A61K 45/06 | (2006.01) | |
| A61K 47/02 | (2006.01) | |
| A61K 9/16 | (2006.01) | |

(56) References Cited

U.S. PATENT DOCUMENTS

| | | | |
|---|---|---|---|
| 4,021,582 A | 5/1977 | Hsu | |
| 4,209,513 A * | 6/1980 | Torode et al. | 514/158 |
| 4,748,161 A * | 5/1988 | Kimura et al. | 514/182 |
| 4,889,720 A * | 12/1989 | Konishi | 424/447 |
| 5,861,141 A * | 1/1999 | Mendizabal | 424/44 |
| 5,932,561 A | 8/1999 | Meyers et al. | |
| 5,942,244 A * | 8/1999 | Friedman et al. | 424/435 |
| 6,087,353 A | 7/2000 | Stewart et al. | |
| 6,110,502 A * | 8/2000 | Burruano et al. | 424/499 |
| 6,139,872 A | 10/2000 | Walsh | |
| 6,197,832 B1 | 3/2001 | Sorkin | |
| 6,352,737 B1 | 3/2002 | Dolhaine et al. | |
| 6,361,800 B1 | 3/2002 | Cooper et al. | |
| 6,376,481 B1 | 4/2002 | Bruce et al. | |
| 6,544,973 B1 | 4/2003 | Miettenen et al. | |
| 6,569,453 B2 | 5/2003 | Linder et al. | |
| 6,576,285 B1 | 6/2003 | Bader et al. | |
| 6,589,588 B1 | 7/2003 | Wester et al. | |
| 6,673,831 B1 | 1/2004 | Tobert | |
| 2001/0034338 A1 | 10/2001 | Sorkin | |
| 2002/0068095 A1 | 6/2002 | Qi et al. | |
| 2002/0103139 A1 | 8/2002 | Weisspapir et al. | |
| 2002/0172721 A1 * | 11/2002 | Boulos et al. | 424/646 |
| 2003/0108591 A1 | 6/2003 | Meijer et al. | |
| 2003/0133965 A1 | 7/2003 | Bruno et al. | |
| 2003/0203854 A1 | 10/2003 | Pischel et al. | |
| 2004/0018248 A1 | 1/2004 | Bendich | |
| 2004/0033202 A1 | 2/2004 | Cooper et al. | |

OTHER PUBLICATIONS

U.S. Appl. No. 14/031,536, filed Jan. 16, 2014, Bubnis et al.

* cited by examiner though it is consistent with this invention and application.

PHYTOSTEROL NUTRITIONAL SUPPLEMENTS

CROSS REFERENCE TO RELATED APPLICATION(S)

This application is a continuation-in-part application that claims priority from U.S. Provisional Application 60/557,247 filed Mar. 29, 2004 entitled "Multi-Vitamin with Phytosterol" and Utility application Ser. No. 11/090,486 filed Mar. 28, 2005 entitled "Multi-Vitamin with Phytosterol" the content of which is incorporated herein in its entirety to the extent that it is consistent with this invention and application.

BACKGROUND OF THE INVENTION

A significant health concern to many individuals is the problem of high cholesterol. While many medications are available for treating this problem, most of the common medications require doctor's supervision for use and are frequently relatively expensive. Certainly a doctor's care and use of these medications in cases of highly elevated or chronically elevated cholesterol are very important but the medications are used when the cholesterol level is a serious health threat.

Some herbal/natural vitamin and/or mineral and/or nutritional compositions that contain phytosterols, compounds that are believed to facilitate cholesterol reduction, are commercially available. However, the efficiency of these herbal/natural product compositions for reducing cholesterol is questionable as they typically contain 20 to 50 mg of phytosterol per dose. This is substantially below the amount that the FDA (Food and Drug Administration) recognizes as an efficacious dose of phytosterol for reducing cholesterol levels. In 21 CFR 101.83, and the FDA sterol enforcement discretion letter dated Feb. 14, 2003, the FDA indicates that 800 mg/day is the lowest effective intake of the phytosterols to reduce risk of coronary heart disease.

In addition to the amount of phytosterol the FDA recommends being a sizable amount of material, phytosterol is a waxy material that is believed to be efficacious in the digestive system in a particulate form. Typically, compressing phytosterol to form a tablet results in formation of a waxy lump or lumps that do not disintegrate in a timely manner. McPherson et al. address the difficulties of tableting free base phytostanols in the Journal of Pharmacy and Pharmacology 2005, 57; 889-896. In order to obtain an efficacious dose of stanols, the authors were forced to split their daily dosage into 6 tablets. The difficulties McPherson encountered in tableting free phytostanols are similar to those encountered when tableting phytosterols.

It would be desirable to have a convenient, practical and relatively inexpensive way to tablet phytosterol for dietary supplementation to facilitate reducing cholesterol levels, and/or reducing homocysteine, and/or decreasing low-density lipoprotein-cholesterol (LDL-C) oxidation in humans before the cholesterol reaches a level to become a serious health threat.

SUMMARY OF THE INVENTION

A nutritional supplement for administration to humans comprising an effective amount of phytosterols and at least one diluent is provided. The diluent is selected from the group consisting of calcium compounds, magnesium compounds, microcrystalline cellulose, starch and a combination thereof. Embodiments of the nutritional supplement that are tableted in swallowable tablets further comprise an absorbent such as silicon dioxide.

The nutritional supplement may be provided as a swallowable tablet in which a daily efficacious amount of nutritional supplement comprises two swallowable tablets and wherein each of the two swallowable tablets has a volume less than about 2 cubic centimeters. In some embodiments the nutritional supplement is a swallowable tablet having an oblong, capsule, modified oval or oval shape. Optionally, the swallowable tablets may be coated with a film coating comprising polyvinyl alcohol.

Alternatively, the nutritional supplement may be provided in a capsule, chewable delivery unit, powder, sachet or suspension form.

A method of nutritional supplementation for a human which facilitates reduction of blood (e.g. serum) cholesterol is provided. The method comprises administering an effective amount of the nutritional supplement disclosed herein to a human.

Further, a method of tableting a nutritional supplement comprising at least one phytosterol in a swallowable tablet is provided. The method includes providing at least one phytosterol and at least one diluent; granulating the phytosterol and the at least one diluent under high shear granulation conditions to form a granulation; milling the granulation; and adding an absorbent to the granulation.

The method may further comprise compressing the granulation to form a tablet. Optionally, the tablet may be coated with a film coat such as a polyvinyl alcohol film coat.

DETAILED DESCRIPTION OF THE INVENTION

Figure 1:
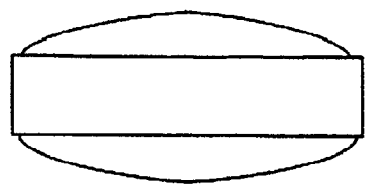
FIG. 1 is an end view of an exemplary embodiment of a tablet of the composition of the invention.

Phytosterols and phytostanols are natural compounds that can be consumed regularly as a part of a healthy diet. Typically, sterols and stanols derived from plant sources are termed phytosterols and phytostanols. Accordingly, while plant derived materials are the preferred source of these compounds, equivalent stanols and sterols synthesized, or from other sources, may be used in the practice of the invention. Any reference to use of phytosterol or phytostanol herein should be taken to apply to equivalent sterols or stanols from alternative sources. It should be understood in terms of discussing amounts of the composition that sterols or phytosterols may be used in like amount or vice-versa. It should be understood in terms of discussing amounts of the composition, that stanols or phytostanols may be used in like amount or vice-versa.

There are multiple specific chemical entities classed as phytosterols, including but not limited to beta-sitosterol, campesterol, and stigmasterol, for example. For the nutritional supplements of this invention either a single specific chemical species of phytosterol or a mixture comprising a plurality of specific chemical species of phytosterol may be employed. For example, a mixture of sterols where approximately 90% of the total material comprises brassicasterol, campesterol, campestanol, stigmasterol, β-sitosterol, Δ-5 avenasterol and β-sitostanol is exemplary of a mixture suitable for use in the practice of the invention. Commercial preparations of mixed phytosterols are available from suppliers such as Cargill, P.O. Box 9300, Minneapolis, Minn. 55440) and ADM (Archer Daniels Midland 4666 Faries Parkway, Decatur, Ill. 62526), for example. Likewise, the class phytostanol includes multiple specific chemical species of phytostanol and a single specific chemical species of phytostanol or a mixture of a plurality of specific chemical species of phytostanol may be used in the practice of the invention. Accordingly, reference to phytosterols or phytostanols in compositions discussed herein should be taken to include both single specific chemical species compositions as well as mixtures of a plurality of species. Phytosterols and phytostanols include free phytosterols and phytostanols and derivatized species such as, for example, esters of phytosterols and phytostanols. In some embodiments free phytosterols or phytostanols are preferred. Further, in some embodiments a mixture of phytosterol and phytostanol may be employed.

Foods such as fruits, vegetables, breads and other whole grain products, and most vegetable oils contain at least some phytosterol. However, it is difficult to consume enough of these foods on a daily basis to obtain sufficient phytosterol intake to have a cholesterol-lowering effect. Based on clinical trial data on the use of phytosterols in the diet, a daily intake of at least 0.8 grams (800 mg) of phytosterols as part of a diet low in saturated fat and cholesterol is recommended by the FDA to provide significant cholesterol lowering benefits. In 21 CFR 101.83, and the FDA sterol enforcement discretion letter dated Feb. 14, 2003, the FDA indicates that 800 mg/day is the lowest effective intake of the phytosterols to reduce risk of coronary heart disease. Consuming the nutritional supplements of this invention is one way to obtain the effective daily intake.

It is believed, but the inventors do not wish to be bound to the theory, that ingested plant sterols and stanols compete with the cholesterol to decrease cholesterol absorption and reabsorption in the small intestine because they are structurally similar to cholesterol. To a point, the more sterol, such as phytosterol, in free form that is present in the intestine following a meal, the less cholesterol absorption and reabsorption will occur. Further, consumed phytosterols, phytostanols, and their equivalents, are not absorbed to any appreciable extent. Hence, phytosterols are believed to inhibit the uptake of cholesterol by the body and are flushed through the system without absorption. One study showed that the overall effect may be an average decline in blood levels of "bad" low-density lipoprotein-cholesterol (the "LDL-C") of 8-15%, with no observed or identified adverse effects. (See "Plant Sterol-Fortified Orange Juice Effectively Lowers Cholesterol Levels In Mildly Hypercholesterolemic Healthy Individuals." Arterioscler. Thromb. Vasc. Biol. 2004 March; 24(3):e25-8; Epub 2004 February, 2005) Preferably, the multi-vitamin and mineral nutritional supplement comprises up to about 3 g of the free form or the esterified form of phytosterols and more preferably at least about 800 mg of phytosterols. Most preferably, the supplement comprises about 800 mg of phytosterols in the free form. In some embodiments the phytosterol may be replaced with phytostanols or a combination of phytosterols and phytostanols may be used.

Phytosterols and phytostanols are waxy materials. When pulverized into a particle size desirable for administration to a human, the material typically is "fluffy" and has a low bulk density. Accordingly, the recommended daily dosage of 800 mg occupies substantial volume. Simply compressing phytosterol into a tablet is problematic as typically, simple compression creates a waxy lump that resists disintegration. As the phytosterol is believed to be most effective in a particulate form in the gut, timely disintegration is believed to be relevant to efficacy.

Accordingly, the present invention is directed to phytosterol and phytostanol compositions that deliver an efficacious dosage of phytosterol and/or phytostanol in a dosage from that is acceptable to a user.

All amounts specified herein are based on milligrams unless otherwise indicated. The term "I.U." represents International Units. The term "mcg" means micrograms, "mg" means milligrams, and "g" means grams. Further, it should be understood that the amounts of components disclosed herein are for a daily dosage and that a daily dosage may comprise one dosage unit or a plurality of dosage units.

"An efficacious dosage" of a nutrient is at least the minimum amount of the nutrient needed on a daily basis recognized by the United States Food and Drug Administration (FDA) for providing a health or nutritional benefit. We further note that in some guidelines the FDA recommends that daily dosages of supplements, such as multivitamin and mineral supplements, be divided and administered in two dosage units taken at spaced intervals during the day. Typically, administration with meals or food is recommended, such as, for example, twice daily with meals. Accordingly, amounts are given for daily dosage, but it should be understood that the daily dosage may be in multiple dosage units and consumption of these units may occur at the same time or different times during the day.

The nutritional supplement of the invention is intended for oral administration and may be provided in a solid form. In addition to the active material, the nutritional supplement may further comprise excipients and processing aides such as: absorbents, diluents, flavorants, colorants, stabilizers, fillers, binders, disintegrants, lubricants, wetting agents, glidants, antiadherents, sugar or film coating agents, preservatives, buffer, artificial sweeteners, natural sweeteners, dispersants, thickeners, antioxidants, solubilizing agents and the like, or some combination thereof.

The nutritional supplement may be formulated in a tablet, capsule, powder or sachet designed for swallowing or may alternatively be formulated as a chewable delivery unit or as a suspension. The daily dosage may be included in a single delivery unit or may comprise multiple delivery units. Dividing the daily dosage among multiple delivery units may be desirable if a tablet is used, for example, to provide a tablet size that is convenient to swallow. If multiple delivery units are used, they may be administered at one time or administered at intervals during the dosage period (e.g. typically a day) if desired. Present FDA guidelines recommend that the daily dosage be divided and administered in two dosage units taken at spaced intervals. However, we note that at least three current clinical studies indicate that once daily dosing of phytosterols is efficacious. (See Plat, J. et al., Effects On Serum Lipids, Lipoproteins and Fat Soluble Antioxidant Concentrations of Consuption Frequency of Margarines and Shortenings Enriched With Plant Sterol Esters., Eur. J. Clin. Nutr. 2000, 54:671-677; Matvienko, O. A. et al., A Single Daily Dose of Soybean Phytosterols in Ground Beef Decreases Serum Total Cholesterol and LDL Cholesterol in Young Mildly Hypercholesterolemeic Men., Am. J. Clin. Nutr. 2002, 76:57-64; and Volpe, R. et al., Effects of Yogurt Enriched With Plant Sterols on Serum Lipids in Patients With Moderate Hypercholesterolemia, British Journal of Nutrition, 2001; 86:233-39).

Accordingly it should be understood that the amounts of the cholesterol reducing agents disclosed herein are for a daily dosage and that dosage may be delivered in a single delivery unit or multiple delivery units. In some embodiments packaging design may be used to facilitate identification of the proper daily dosage to the consumer. For example, a blister pack with labeling to indicate a daily dosage or a sachet pocket with a daily dose or fraction thereof so labeled may be used.

Tableting compositions containing phytosterol presents challenges. Phytosterol has a waxy nature, is hydrophobic, typically does not flow well in micronized form and has a low bulk density. These properties cause problems during the tablet making (tableting) process, which include but are not limited to, picking and sticking of materials to tooling, materials sticking to the press turntable during compression and poor tablet weight control. Further, phytosterol is difficult to mill because it tends to clog the mill screen unless cryo-milled. Prior to the present invention, tablets high in phytosterol typically exhibited poor compressibility and once compressed had slow tablet disintegration adversely impacting delivery of the phytosterol upon ingestion. Timely disintegration is believed to be important for efficacy, as inventors believe, without wishing to be held to the theory, that phytosterol acts in primary particle form in the gastrointestinal lumen.

The inventors have surprisingly discovered that use of certain granulating methods can yield a swallowable tablet containing at least one half the daily efficacious dose of phytosterol in a single tablet, which is a size that may be swallowed by a human. Further, the tablet of the invention disintegrates into primary particles in a time consistent with gastric emptying time, e.g. the compacted phytosterol containing tablet of the invention is believed to substantially disintegrate before reaching the gastrointestinal lumen. In an embodiment in which a daily efficacious dose of the nutritional supplement is contained in two tablets, it is preferable that the volume of each tablet is less than about 2 cubic centimeters.

In another embodiment an efficacious daily dose of the nutritional supplement of the invention is tableted in four swallowable tablets or less each of a size that can be swallowed by a human. Preferably when a daily efficacious dosage is contained in three or four tablets each tablet has a volume of about 1.5 cubic centimeters or less.

Figure 2:
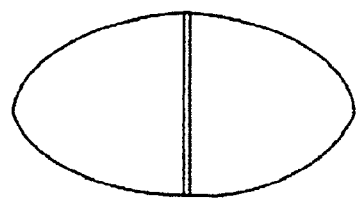
FIG. 2 is a top view of an exemplary embodiment of a tablet of the composition of the invention.
Figure 3:
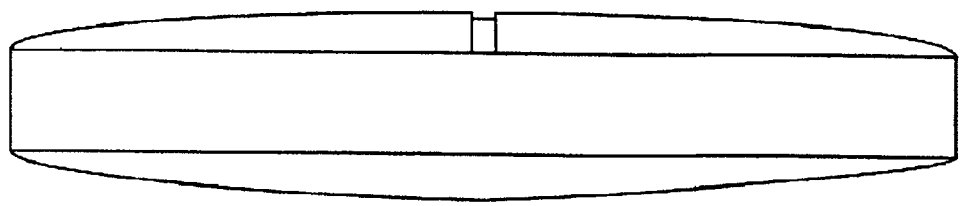
FIG. 3 is a side view of an exemplary embodiment of a table of the composition of the invention.

Tablet shape of a nutritional supplement swallowable tablet is believed to contribute to several factors that may improve user compliance particularly for large swallowable tablets. The inventors believe without wishing to be held to the theory, that oblong, oval, modified oval, and capsule shaped compacts of about 1.5 cubic centimeters in volume or less, for example, are easier for a consumer to swallow than round compacts of about 1.5 cubic centimeters or less, for example. Tablets that are easier to swallow may improve user compliance with the dosing regimen in some instances. Accordingly, is some embodiments of swallowable tablets, it may be desirable to use an oblong, oval modified oval or capsule shape for the tablet. FIGS. 1 to 3 show an exemplary embodiment of a tablet shape. As one skilled in the art will appreciate, this shape is exemplary and any of many other shapes may be equally suitable in the practice of the invention.

The phytosterol compositions may be prepared using granulation methods. For embodiments in which the composition is formed into a swallowable tablet, it may be desirable to mix the phytosterol with an absorbent prior to granulation. Alternatively, the absorbent may be mixed with the granulation prior to tableting the swallowable tablets. Silicates such as calcium silicate or silicon dioxide or other absorbents such as talc or titanium dioxide may be used, for example. The absorbent helps maintain the phytosterol in a particulate form by inhibiting the clumping of phytosterol particles into waxy lumps during processing and tableting. The inventors, believe without wishing to be bound to the theory that their discovery of coating or partially coating the phytosterol with silicon dioxide diluent and/or absorbent before or after the granulation process produces granules that may be used to form a swallowable tablet, which disintegrates in a timely manner. Thus, the inventors'discovery addresses the problem of untreated waxy phytosterols tending to form compacts with undesirably long disintegration times (e.g. compacted compounds that are likely to pass through the gastrointestinal track with minimum, if any, disintegration to primary particles which are believed to be necessary for efficacy).

The inventors further believe that the physical nature and size of the absorbent particle may modify the disintegration rate of the tablet. For example, the inventors have discovered that when the absorbent silicon dioxide was used at a 1:8 w/w ratio with phytosterols, slower disintegration was seen with a fumed silicon dioxide of about 0.2-0.3 micron particle size and about 200 meters squared per gram surface area than with a precipitated silicon dioxide of about 7 micron particle size and about 300 meters squared per gram surface area. The inventors believe that it is preferable to use precipitated silicon dioxide as described above as the absorbent for an immediate release phytosterol nutritional supplement and that a fumed silicon dioxide as described above as the absorbent may be used to modulate disintegration rate. As the physical nature and size of the absorbent appear to impact the rate of disintegration in some embodiments, it may be desirable to use a mixture of types of absorbent and/or particle size of absorbent particles to facilitate obtaining the desired disintegration profile.

Figure 4:
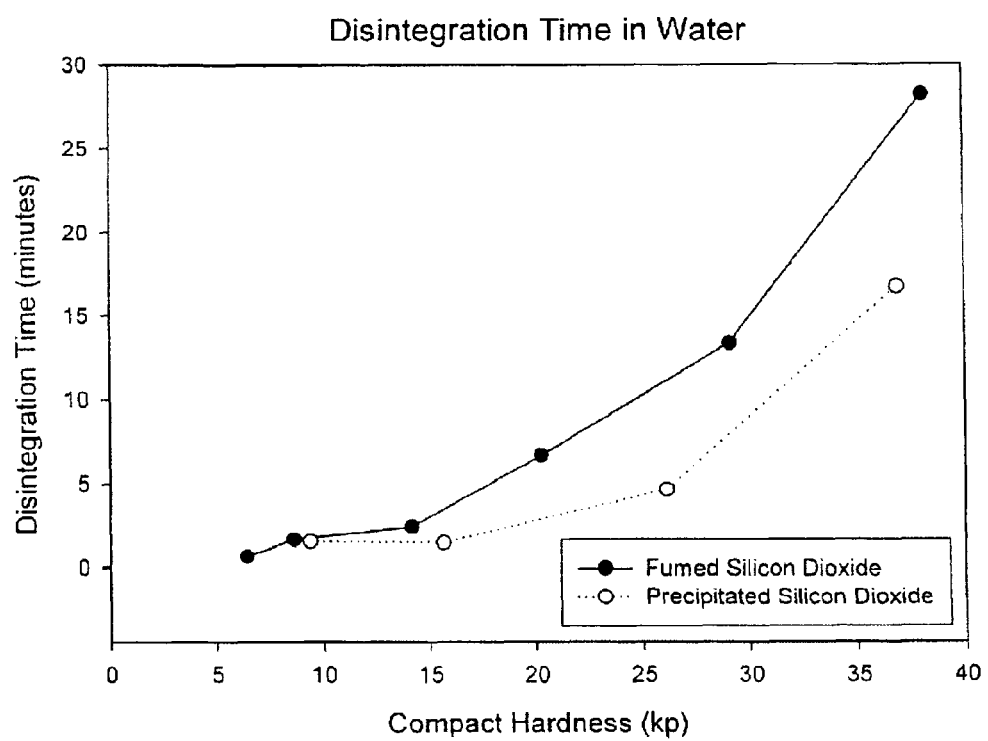
FIG. 4 is a graph showing tablet disintegration data for tablets of exemplary embodiments of the composition of the invention in water.
Figure 5:
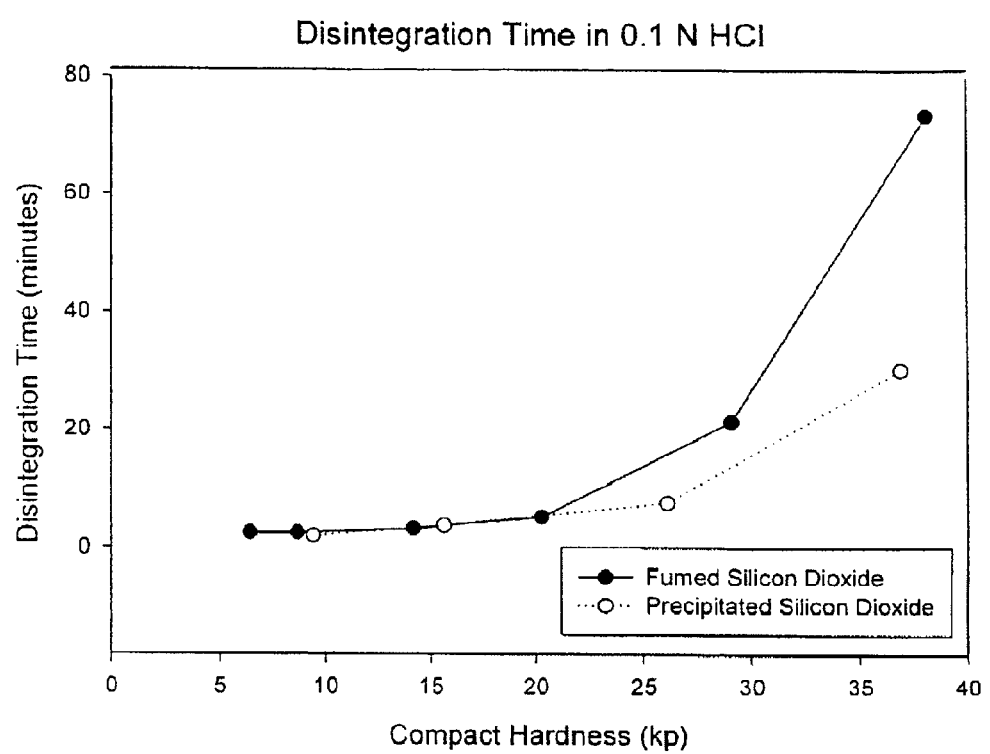
FIG. 5 is a graph showing tablet disintegration data for tablets of exemplary embodiments of the invention in acid.

FIGS. 4 and 5 show exemplary disintegration data for two examples of tableted phytosterol compositions of the invention granulated and tableted as described herein. FIGS. 4 and 5 show disintegration in water and acid, respectively. All examples in FIGS. 4 and 5 have disintegration times compatible with the timely disintegration in the gastrointestinal track. However, times do vary depending on the form of silicon dioxide used as FIGS. 4 and 5 show.

In one embodiment the composition may be prepared using a high shear wet-granulation method. In an exemplary high shear wet granulation method phytosterol (or phytosterol treated with absorbent) is granulated with at least one diluent. The diluent may comprise one or more inorganic mineral nutrients, such as, for example, a magnesium compound, or calcium compound; other active agents; and/or inactive diluents such as, for example celluloses, cellulose derivatives, lactose or other sugars, polyols, starches, starch derivatives, polymers or mixtures thereof. Utilizing one or more high-density inorganic mineral nutrients as the diluent or a portion of the diluent has the advantage of minimizing added excipients and facilitates forming a smaller tablet. Dibasic calcium phosphate, and magnesium oxide are exemplary of specific high-density compounds, which are useful as diluents or a portion of the diluents. These diluents are exemplary and other diluents and granulation components or mixtures thereof known to those skilled in the art may be used for the granulation.

Other granulation excipients known to those skilled in the art may be added such as povidone, disintegrants, co-disintegrants, super-disintegrants, surfactants, glidants, lubricants and binders. In one exemplary embodiment (a mixture of inorganics minerals and microcrystalline cellulose), the mixture subjected to granulation comprised the phytosterol, diluents the binder polyvinyl pyrrolidone (PVP), the excipient crospovidone, and water. The water was added slowly to the remaining ingredients while they were mixed in a high-shear granulator.

Optionally, the granulation may be dried. The drying may be performed in a fluid bed dryer, for example. The granulation is milled to a suitable particle size. In one exemplarily embodiment a 0.05 screen was used. However, as one skilled in the art will appreciate this is exemplary and other sizes may be employed.

Optionally, after milling, the milled granulation may be mixed with an absorbent. Silicon dioxide, silicon dioxide, talc and titanium dioxide are exemplary of suitable absorbents. Other materials known to these skilled in the art as absorbents may also be used in the practice of the invention.

Other components may be blended into the milled granulation with the absorbent preferably in an ordered blending after a portion of the absorbent is combined with the granulation. These additional components may be added as single ingredients, preformed mixes or a combination thereof. Other excipients such as flavorants, colorants, stabilizers, fillers, binders, disintegrants, lubricants, milling agents, glidants, antiadherents, preservatives, buffers, sweeteners, dispersants, thickness, solubilizing agent and the like or same combination thereof may optionally be included.

After blending, the composition may be formed into tablets using compression methods, for example. Optionally, the tablets may be coated using tablet coating materials and methods such as those known to those skilled in the art. The waxy nature of the sterols has been discovered to make adherence of a film-coating material to the tablet more difficult. The inventors have discovered that satisfactory adherence may be obtained using an aqueous based film-coating system comprising polyvinyl alcohol. Further, the inventors believe without wishing to be held to the theory, that using a film-coating comprising polyvinyl alcohol may improve patient compliance by yielding a tablet that is easier to swallow.

The high shear granulation method described herein is exemplary of a suitable method for preparing the composition of the invention. The inventors also note that the wet granulation method described herein does not require expensive cryo-milling. Alternatively, methods such as dry slugging, dry roller compaction or extrusion could be used to prepare the compositions of the invention.

Optionally, the granulation may be filled into a capsule or provided as a powder or sachet. If packaged as a powder or sachet it may be provided in a bulk container or individual packets contain a daily dosage or some fraction thereof, for example.

Alternatively, in another embodiment of the invention the composition may be prepared as a chewable tablet. The phytosterol active may be combined with sweetener, flavorants and processing aids suitable for a chewable tablet and tableted as a chewable tablet. A chewable tablet will typically comprise a phytosterol granulation in combination with a sweetener or sweeteners and a flavoring. A phytosterol granulation, such as for example, the one described for the swallowable tablet may be used as the phytosterol granulation. Exemplary sweeteners include, but are not limited to, natural sweeteners such as sucrose, fructose, xylitol, dextrose, mannitol, or combinations thereof, for example; artificial sweeteners such as sucralose, aspartame, acesulfame potassium, neotame, or combinations thereof, for example. Mixtures of sweeteners may be used including a combination of natural and artificial sweeteners as well as different specific sweeteners. Typically, a chewable tablet is not coated with a film-forming polymer, however elimination of the film coating is not required. Optionally, a non-micronized particle size/prilled phytosterol and or phytostanol may be used in place of the micronized particle size phytosterol, since the chewable tablet is designed to be masticated during consumption resulting in particle size reduction. Use of silicon dioxide in the chewable tablet to decrease disintegration time is likewise optional due to mastication during consumption.

In another embodiment, the phytosterol composition may be prepared as an aqueous suspension and administered as a liquid dosage form. This dosage form is preferred by some consumers who have difficulty swallowing tablets. A suspension formulated using a structured vehicle approach based on bentonite may be used, for example, other suspension formulation approaches as known to those skilled in the art may likewise be suitable.

EXAMPLE 1

Nutritional Supplement Granulation

The composition of an exemplary embodiment of the invention is provided in Table 1. This composition is representative of a composition within the scope of the invention and is provided for illustrative purposes. The nutritional supplement of Example 1 is intended to be a daily dosage and typically would be administered in one or more dosage units (e.g. one to four tablets). If multiple dosage units are used, the multiple units may be taken at one time or at spaced intervals during the day. The composition may be tableted, filled into a capsule, or packaged as a sachet.

TABLE 1

| Micronized Sterol Granulation Based Swallowable Tablet | |
| --- | --- |
| Ingredient | Amount/Daily |
| Granulation Ingredients | |
| Micronized Phytosterol | 800 mg. |
| Dicalcium Phosphate | 220 mg. |
| Magnesium Oxide | 71 mg. |
| Zinc Oxide | 10 mg |
| Microcrystalline Cellulose | 268 mg. |
| Polyvinyl pyrrolidone | 143 mg. |
| Croscarmellose | 36 mg. |
| Crospovidone | 30 mg. |
| Extra-granular ingredients | |
| Microcrystalline Cellulose | 200 mg |
| Magnesium Stearate | 40 mg |
| Croscarmellose | 36 mg |
| Crospovidone | 30 mg |
| Dicalcium Phosphate | 200 mg |

EXAMPLE 2

Method of Preparing a Swallowable Tableted Nutritional Supplement

Embodiment of one exemplary swallowable tablet nutritional supplement of the invention was prepared by the method included first delumping the phytosterol using a low energy oscillation system equipped with a screen. The delumped phytosterol was then transferred to a high shear granulator and combined with MgO, and dibasic calcium phosphate diluents, ZnO, microcrystalline cellulose, super disintegrant and polyvinyl pyrrolidone binder were added to the granulation bowl. Granulation was begun with a low speed blending and water was added gradually with mixing to form an acceptable granulation. One skilled in the art is familiar with the appearance and physical characteristics of an acceptable granulation.

Once an acceptable granulation was obtained the granulation was dried in a fluid bed dryer with air at an airflow inlet temperature of about 90° C. The granulation was dried to moisture content of not more than about 1.5% w/w as determined by an infrared loss on drying balance.

The dried granulation was cooled and milled at a medium speed, with knives forward using a 0.050 inch screen. Approximately half of the milled granulation was put into a slant cone blender, followed by #20 mesh screened silicon dioxide. The remainder of the milled granulation was added and the mixture was blended.

The granulation thus obtained was compressed into tablets using tableting techniques known to those skilled in the art using a tablet tooling with an oval shape. The inventors believe that oblong, modified oval, and capsule shaped compacts may be easier for a consumer to swallow than round compacts of similar volume. In this embodiment a daily efficacious dosage of phytosterol and the indicated vitamins and minerals was tableted in two tablets each tablet having a volume of about 1.2 cm$^3$.

The tablets were then coated using an aqueous based film-coating system comprising polyvinyl alcohol.

The composition of Table 1 is likewise suitable for filling into a capsule or packaging as a sachet.

EXAMPLE 3

Chewable Tablet Composition

The composition of another exemplary embodiment of the invention is provided in Table 2. The composition is tableted as a chewable tablet.

TABLE 2

Micronized Sterol Granulation based Chewable Tablet Composition

| Ingredient | mg/daily dosage |
|---|---|
| Granulation Ingredients | |
| Micronized Phytosterol | 800 mg. |
| Dicalcium Phosphate | 226 mg. |
| Magnesium Oxide | 71 mg. |
| Zinc Oxide | 10 mg. |
| Microcrystalline Cellulose | 208 mg. |
| Polyvinyl pyrrolidone | 142 mg. |
| Croscarmellose | 36 mg. |
| Crospovidone | 30 mg. |
| Extra-granular Ingredients | |
| Microcrystalline Cellulose | 205 mg. |
| Magnesium Stearate | 41 mg. |
| Citric Acid | 42 mg. |
| Xylitol | 2000 mg. |
| Flavorant* | <3% wt/wt |

*The flavorant may be a single flavorant or mixture of flavorants.

EXAMPLE 4

Chewable Tablet Composition

The composition of another exemplary embodiment of the invention is provided in Table 3. The phytosterol active of the composition of Table 3 has a non-micronized particle size (e.g. prilled phytosterol in place of the micronized particle size phytosterol). Since the chewable tablet is designed to be masticated during consumption the desirable particle size reduction may be achieved by mastication. The composition is tableted as a chewable tablet.

TABLE 3

Non-Micronized Sterol based Chewable Tablet Composition

| Ingredient | % wt/wt |
|---|---|
| Non-micronized Phytosterols | 28% |
| Microcrystalline Cellulose | 5% |
| Xylitol | 58% |
| Crospovidone | 3% |
| Silicon Dioxide | 3% |
| Magnesium Stearate | 0.75% |
| Flavorant* | 1.5% |
| Colorants* | <3% |
| | <1% |

*A single flavorant may be used as a mixture of flavors, likewise a single colorant or mixture of colorants may be used.

EXAMPLE 5

Suspension Composition

The composition of another exemplary embodiment of the invention is provided in Table 4. The composition of Table 4 is a suspension.

TABLE 4

Suspension Composition

| Ingredient | % w/v |
|---|---|
| Micronized Sterol | 14.2% |
| Bentonite | 1.8% |
| Sodium Citrate Dihydrate | 0.68% |
| Citric Acid | 0.19% |
| Sucralose | 0.12% |
| Sodium Benzoate | 0.02% |
| Colorant | 0.01% |
| Flavorant | 0.08% |
| Water | 82.72% |

Although the foregoing invention has been described in some detail by way of illustration and examples for purposes of clarity of understanding it will be obvious that certain changes and modifications may be practiced within the scope of the appended claims. Modification of the above-described modes of practicing the invention that are obvious to persons of skill or the art are intended to be included within the scope of the following claims.

What is claimed is:

1. An immediate release nutritional supplement for administration to humans comprising: an effective amount of phytosterol and a second element; wherein the phytosterol is mixed with at least part of the second element prior to blending with other suitable ingredients, resulting in a phytosterol that is at least partially coated with the second element; wherein the second element consists of at least one absorbent and the at least one absorbent comprises silicon dioxide; wherein the nutritional supplement is a swallowable tablet; and wherein there are no surfactants in the tablet of the nutritional supplement.

2. The immediate release nutritional supplement of claim 1, wherein the second element further comprises calcium silicate, talc, titanium dioxide, and combinations thereof.

3. The nutritional supplement of claim 1, wherein the tablet is coated with a film coating comprising polyvinyl alcohol.

4. A method of a nutritional supplementation for a human which facilitates reduction of serum cholesterol comprising providing a human an effective amount of the nutritional supplement of claim 1.

5. A method of tableting an immediate release phytosterol containing nutritional supplement, said method comprising: providing at least one phytosterol; forming phytosterol particulates of a suitable particle size; mixing the phytosterol particulates with a second element prior to blending other suitable ingredients with the phytosterol particulates; and then tableting the blend; wherein the second element consists of at least one absorbent and the at least one absorbent comprises silicon dioxide; and wherein there are no surfactants in the tablet of the nutritional supplement.

6. The method of claim 5 wherein the tableted immediate release phytosterol further comprises a diluent, wherein at least a portion of the diluent is selected from a calcium compound and a magnesium compound or a mixture thereof.

7. The method of claim 5 wherein the second element further comprises calcium silicate, talc, titanium dioxide, and combinations thereof.

8. The method of claim 5, said method further comprising film coating the tablet.

9. An immediate release phytosterol containing nutritional supplement prepared by the process comprising the steps of:
 (a) providing at least one phytosterol;
 (b) forming phytosterol particulates of a suitable particle size;
 (c) mixing the phytosterol particulates with a second element prior to step (d);
 (d) blending other suitable ingredients with the phytosterol particulates of step (c);
 and then
 (e) tableting the blend of step (d);
wherein the second element consists of at least one absorbent and the at least one absorbent comprises silicon dioxide: and wherein there are no surfactants in the tablet of the nutritional supplement.

10. The nutritional supplement of claim 9 wherein the tableted immediate release phytosterol further comprises a diluent, wherein at least a portion of the diluent is selected from a calcium compound and a magnesium compound or a mixture thereof.

11. The nutritional supplement of claim 9 wherein the second element further comprises calcium silicate, talc, titanium dioxide, and combinations thereof.

* * * * *